United States Patent
Seth et al.

(10) Patent No.: US 10,497,114 B2
(45) Date of Patent: Dec. 3, 2019

(54) METHOD AND APPARATUS FOR CERVICAL IMAGE ANALYSIS WITH IMPROVED RELIABILITY

(71) Applicant: KONINKLIJKE PHILIPS N.V., Eindhoven (NL)

(72) Inventors: Subhendu Seth, Bangalore (IN); Pallavi Vajinepalli, Bangalore (IN); Payal Keswarpu, Elmsford, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 670 days.

(21) Appl. No.: 15/109,154

(22) PCT Filed: Dec. 17, 2014

(86) PCT No.: PCT/EP2014/078181
§ 371 (c)(1),
(2) Date: Jun. 30, 2016

(87) PCT Pub. No.: WO2015/101496
PCT Pub. Date: Jul. 9, 2015

(65) Prior Publication Data
US 2016/0328845 A1  Nov. 10, 2016

(30) Foreign Application Priority Data
Dec. 30, 2013  (EP) .................................. 13199747

(51) Int. Cl.
*G06T 7/00* (2017.01)
*A61B 5/00* (2006.01)
*A61M 5/00* (2006.01)

(52) U.S. Cl.
CPC .......... *G06T 7/0012* (2013.01); *A61B 5/4331* (2013.01); *A61M 5/007* (2013.01);
(Continued)

(58) Field of Classification Search
CPC . A61B 5/4331; A61B 2576/00; A61B 5/0059; A61M 5/007; G06T 7/0012;
(Continued)

(56) References Cited

U.S. PATENT DOCUMENTS 8,068,694 B2  11/2011  Zhang et al.
2009/0034824 A1  2/2009  Li et al.
(Continued)

FOREIGN PATENT DOCUMENTS

RU  2240041 C1  11/2004
WO  2012123881 A2  9/2012
WO  WO 2012/123881 A2 *  9/2012

OTHER PUBLICATIONS

Seth, "Nucleus Segmentation in Pap-Smear Images", Phiilps Research, ICBME, 2011, 1 Page Abstract.
(Continued)

*Primary Examiner* — Edward Park

(57) ABSTRACT

The invention relates to a method and an apparatus for cervical image analysis, wherein a transformation zone is identified in an acetic acid image by registering with its Lugol's iodine counterpart. Then, regions in the transformation zone which show significant changes in whiteness are identified as aceto-white regions and registered with the corresponding Lugol's iodine image, and it is determined if the identified regions in the Lugol's iodine image are iodine negative or positive. Based thereon, the aceto-white region can be categorized as one of metaplasia, inflammation or premalignant lesion region.

10 Claims, 4 Drawing Sheets

(52) U.S. Cl.
CPC ......... *A61B 5/0059* (2013.01); *A61B 2576/00* (2013.01); *G06T 2207/10016* (2013.01); *G06T 2207/10024* (2013.01); *G06T 2207/30096* (2013.01)

(58) Field of Classification Search
CPC . G06T 2207/10016; G06T 2207/10024; G06T 2207/30096
See application file for complete search history.

(56) References Cited

U.S. PATENT DOCUMENTS

2010/0092064 A1    4/2010   Li
2014/0005477 A1    1/2014   Gupta et al.

OTHER PUBLICATIONS

Arganda-Carreras, "Consistent and Elastic Registration of Histological Sections Using Vector-Spline Regularization", Computer Vision Approaches to Medical Image Analysis, Springer, 2006, pp. 85-95.

Goparaju et al, "A Fast Hierarchical Multilevel Image Segmentation Method Using Unbiased Estimators", CoRR-Computing Research Respository, 2007, pp. 10.

Pallavi et al, "Automated Analysis of Cervix Images to Grade the Severity of Cancer", Engineering in Medicine and Biology Society, 2011, pp. 3439-3442.

Kulinich S. et al., "The role of colposcopy in the differential diagnosis of infectious diseases of the cervix", Far Eastern Medical Journal, 2009, pp. 48-51.

\* cited by examiner

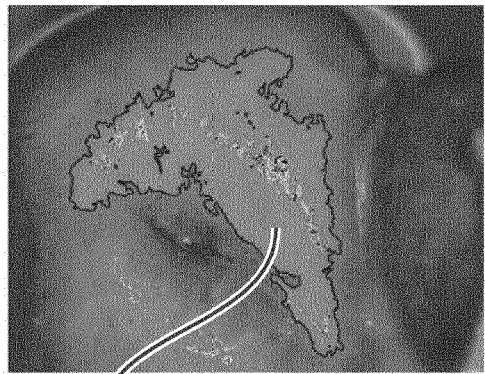
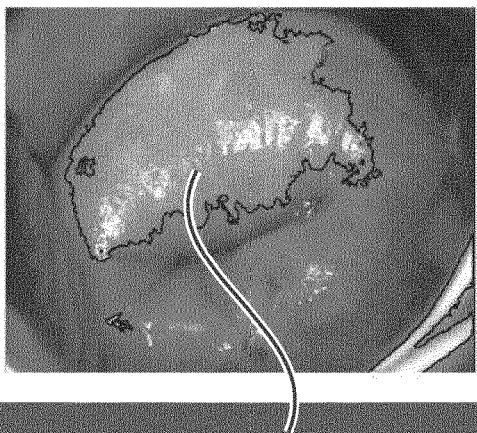
FIG. 5A  FIG. 5B
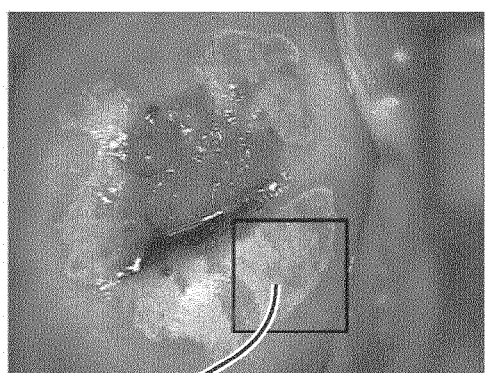
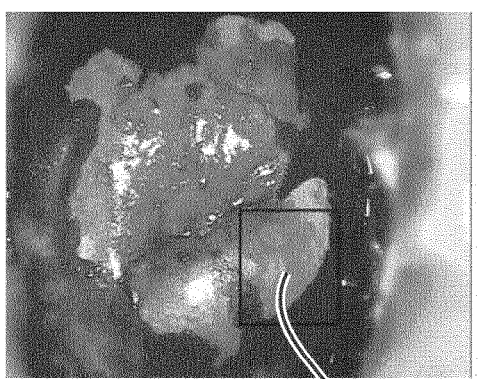
FIG. 6A  FIG. 6B

METHOD AND APPARATUS FOR CERVICAL IMAGE ANALYSIS WITH IMPROVED RELIABILITY

CROSS-REFERENCE TO PRIOR APPLICATIONS

This application is the U.S. National Phase application under 35 U.S.C. § 371 of International Application No. PCT/EP2014/078181, filed on Dec. 17, 2014, which claims the benefit of European Patent Application No. 13199747.0, filed on Dec. 30, 2013. These applications are hereby incorporated by reference herein.

FIELD OF THE INVENTION

The invention relates to the field of apparatuses and methods for semi-automated or automated aceto-whiteness region detection, representation and quantification for any automated cervical image analysis systems.

BACKGROUND OF THE INVENTION

When cells are faced with physiological or pathological stresses, they respond by adapting in any of several ways, one of which is metaplasia. It is a benign (i.e. non-cancerous) change that occurs as a response to change of milieu (physiological metaplasia) or chronic physical or chemical irritation (pathological metaplasia). One example of pathological irritation is cigarette smoke that causes the mucus-secreting ciliated pseudostratified columnar respiratory epithelial cells that line the airways to be replaced by stratified squamous epithelium, or a stone in the bile duct that causes the replacement of the secretory columnar epithelium with stratified squamous epithelium (Squamous metaplasia). Thus, metaplasia refers to the change or replacement of one type of epithelium by another. More specifically, metaplasia is an adaptation that replaces one type of epithelium with another that is more likely to be able to withstand the stresses it is faced with. It is also accompanied by a loss of endothelial function, and in some instances considered undesirable. This undesirability is underscored by the propensity for metaplastic regions to eventually turn cancerous if the irritant is not eliminated.

The medical significance of metaplasia is that in some sites where pathological irritation is present cells may progress from metaplasia, to develop dysplasia, and then malignant neoplasia (cancer). Thus, at sites where abnormal metaplasia is detected, efforts are made to remove the causative irritant, thereby decreasing the risk of progression to malignancy.

In the field of cervical image analysis, a transformation zone (TZ) is an area in the uterine cervix, where columnar epithelium is replaced by squamous epithelium. This is the region where the cancer occurs in the uterine cervix. During a colposcopy procedure, a 3-5% acetic acid solution is applied to the cervix. Acetic acid causes cellular dehydration and reversible coagulation of intracellular proteins, thus reducing the transparency of the epithelium. This results in temporary whiteness of the epithelium, i.e., aceto-white epithelium.

The speed with which this whiteness appears and disappears depends on the number of cells, amount of cytoplasm and nucleus size. Unfortunately, not all the areas of aceto-white epithelium indicate the presence of premalignant disease, for example areas of metaplastic epithelium are also aceto-white.

Following application of acetic acid, 3-5% of Lugol's iodine stain is used. Lugol's iodine, also known as Lugol's solution is a solution of elemental iodine and potassium iodide in water, named after the French physician J. G. A. Lugol. Lugol's iodine solution is often used as an antiseptic and disinfectant, for emergency disinfection of drinking water, and as a reagent for starch detection in routine laboratory and medical tests. These uses are possible since the solution is a source of effectively free elemental iodine, which is readily generated from the equilibration between elemental iodine molecules and triiodide ions in the solution. Normal squamous epithelium is rich in glycogen and stains dark brown with iodine (iodine positive), whereas premalignant squamous epithelium and endo-cervical epithelium is deficient in glycogen and does not stain to iodine (iodine negative). However, the mature metaplastic epithelium in most women is glycogen rich and stains dark brown to Lugol's iodine.

Aceto-whiteness detection, representation and quantification are important features of any automated cervical image analysis systems. However, not only the premalignant lesions but also the immature metaplasia shows aceto-white characteristics. This causes undesirable false alarms for aceto-white regions in automated colposcopic image analysis systems.

SUMMARY OF THE INVENTION

It is an object of the present invention to provide an improved automated image analysis, by means of which false alarms for aceto-white regions can be reduced.

Accordingly, false alarms for aceto-white regions in automated image analysis systems can be reduced or isolated by using multi-stained image registration between acetic acid and Lugol's iodine image. A transformation zone is identified in an acetic acid image by registering with an iodine counterpart image of the acetic acid image. Then, a region with more than a predetermined minimum change in whiteness is identified within the transformation zone and the identified region is registered with the iodine counterpart image. Based on the registration of the identified region with the iodine counterpart image, it is decided on a type of iodine uptake of the identified region so as to determine if the identified region comprises a premalignant lesion.

According to a first option, transformation zones registered in pre acetic acid and post acetic acid images may be used, e.g. by the zone identifier of claim 1, to identify the region with more than a predetermined minimum change in whiteness due to application of acetic acid. This measure helps in propagating anatomical segmentation of different anatomical regions across different stains.

According to a second option which can be combined with the first option, color values of an initial color space (e.g. RGB color space) of the transformation zone in the post acetic acid images may be converted, e.g. by the aceto-white identifier of claim 1, to a color space with a color component (e.g., the L component of the Lab color space) that substantially matches human perception of lightness or whiteness. This ensures that proper discrimination in accordance with human perception can be achieved.

According to a third option which can be combined with the first or second option, pixels in the identified transformation zone may be clustered, e.g. by the aceto-white identifier of claim 1, based on their opacity change and pixels with an opacity change below a predetermined threshold may be removed. Thereby, a straight forward discrimination among dominant and minor opacity changes can be achieved.

According to a fourth option which can be combined with any one of the above first to third options, clustering based multilevel histogram thresholding may be applied inside the identified transformation zone, e.g. by the aceto-white identifier of claim 1. This measure helps in finding the desired result iteratively According to a fifth option which can be combined with any one of the above first to fourth options, information gain based aceto-white region selection my be applied, e.g., by the aceto-white identifier of claim 1. Thereby, a suitable termination criterion for the above histogram thresholding can be obtained to isolate varied homogeneous regions.

According to a sixth option which can be combined with any one of the above first to fifth options, a change of intensity of a foreground to background ratio of a post acetic acid image may be compared, e.g. by the aceto-white identifier of claim 1, with that of a pre acetic acid counterpart image. Thereby, aceto-white regions may readily be identified.

According to a seventh option which can be combined with any one of the above first to sixth options, a histogram of red channel values of the iodine counterpart image may be generated, peaks of the histogram may be identified, and the type of iodine uptake may be decided based on a threshold at a second peak of the histogram, e.g. by the region separator of claim 1. Thus, iodine uptake can be identified and categorized.

It is noted that the above apparatus may be implemented based on discrete hardware circuitry with discrete hardware components, an integrated chip, or an arrangement of chip modules, or based on a signal processing device or chip controlled by a software routine or program stored in a memory, written on a computer readable medium, or downloaded from a network, such as the Internet.

It shall be understood that a preferred embodiment of the invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIGS. 5A and 5B show exemplary results of detected aceto-white regions; and

FIGS. 6A and 6B show exemplary results of identified iodine uptake by registering aceto-white regions in a Lugol's iodine image.

DETAILED DESCRIPTION OF EMBODIMENTS

Figure 1:
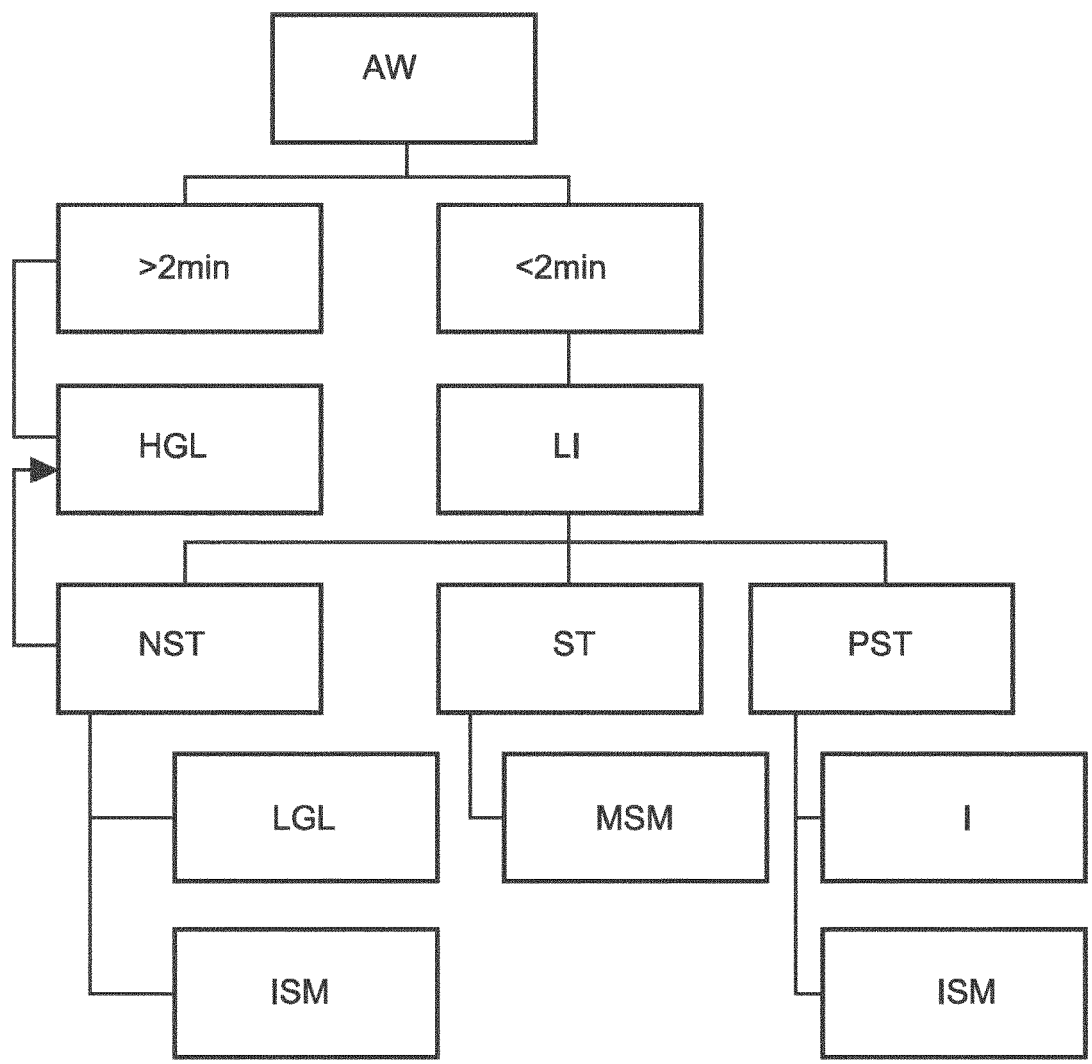
FIG. 1 shows a block based representation of aceto-white characteristics.

Embodiments of the present invention are now described based on an automated colposcopic image analysis system.

Colposcopic practice includes the examination of features of the cervical epithelium after application of saline, 3-5% dilute acetic acid, and Lugol's iodine solution in successive steps. The study of the vascular pattern of the cervix may prove difficult after application of acetic acid and iodine solutions. Hence the application of physiological saline before acetic acid and iodine application is useful in studying the subepithelial vascular architecture in great detail.

The 3-5% acetic acid is usually applied with a cotton applicator (e.g. cotton balls held by sponge forceps, or large rectal or small swabs) or with a small sprayer. It helps in coagulating and clearing the mucus. Acetic acid is thought to cause swelling of the epithelial tissue, columnar and any abnormal squamous epithelial areas in particular. It causes a reversible coagulation or precipitation of the nuclear proteins and cytokeratins. Thus, the effect of acetic acid depends upon the amount of nuclear proteins and cytokeratins present in the epithelium. When acetic acid is applied to normal squamous epithelium, little coagulation occurs in the superficial cell layer, as this is sparsely nucleated. Though the deeper cells contain more nuclear protein, the acetic acid may not penetrate sufficiently and, hence, the resulting precipitation is not sufficient to obliterate the colour of the underlying stroma. Areas of cervical intraepithelial neoplasia (CIN) undergo maximal coagulation due to their higher content of nuclear protein and prevent light from passing through the epithelium. As a result, the subepithelial vessel pattern is obliterated and less easy to see and the epithelium appears white. This reaction is termed aceto-whitening, and produces a noticeable effect compared with the normal pinkish colour of the surrounding normal squamous epithelium of the cervix, an effect that is commonly visible to the naked eye.

Furthermore, the principle behind the iodine test is that original and newly formed mature squamous metaplastic epithelium is glycogenated, whereas CIN and invasive cancer contain little or no glycogen. Columnar epithelium does not contain glycogen. Immature squamous metaplastic epithelium usually lacks glycogen or, occasionally, may be partially glycogenated. Iodine is glycophilic and hence the application of iodine solution results in uptake of iodine in glycogen-containing epithelium. Therefore, the normal glycogen-containing squamous epithelium stains mahogany brown or black after application of iodine. Columnar epithelium does not take up iodine and remains unstained, but may look slightly discoloured due to a thin film of iodine solution. Areas of immature squamous metaplastic epithelium may remain unstained with iodine or may be only partially stained. If there is shedding (or erosion) of superficial and intermediate cell layers associated with inflammatory conditions of the squamous epithelium, these areas do not stain with iodine and remain distinctly colourless in a surrounding black or brown background. Areas of CIN and invasive cancer do not take up iodine (as they lack glycogen) and appear as thick mustard yellow or saffron-coloured areas.

FIG. 1 shows a block based representation of aceto-white characteristics. If aceto-whiteness appears fast and lasts long (e.g. for more than 2 min), then a high grade lesion (HGL) can be assumed. Otherwise, if aceto-whiteness appears slowly and disappears quickly (e.g. after less than 2 min), application of Lugol's iodine provides different results of stain depending on the conditions of the epithelium. If no stain (NST) is observed, than high grade lesion (HGL) or low grade lesion (LGL) or immature squamous metaplasia (ISM) can be assumed. If stain (ST) is observed, than mature squamous metaplasia (MSM) can be assumed. Finally, if partial stain (PST) is observed, than inflammation (I) or immature squamous metaplasia (ISM) can be assumed.

The following embodiments are based on the above aceto-white characteristics by applying an analysis where the transformation zone (TZ) is identified in acetic acid images by registering with its Lugol's iodine counterpart. This process is eminent as this will restrict the remaining part of the proposed automated image analysis to the TZ region which is the most probable area for malignant activities. Then, an aceto-white probable region is identified in the TZ, i.e., a region of the TZ, which shows significant changes in whiteness. Identified aceto-white regions are registered (or aligned) in the acetic acid image with a corresponding Lugol's iodine image. Based on the registered images, iodine uptake and FP reduction are assessed and characterized. This can be achieved by determining if the corresponding region in the Lugol's iodine image is iodine negative or positive, and based thereon determining if the aceto-white region is metaplasia, inflammation or a premalignant lesion.

Demarcation of the TZ by registering both the acetic-acid and Lugol's iodine images is a challenging task, as both of them exhibit different colours and textural appearances. In the following, procedures for efficient demarcation of the aceto-white region and cross-checking the information from its Lugol's iodine counterpart are described based on first to third embodiments.

Figure 2:
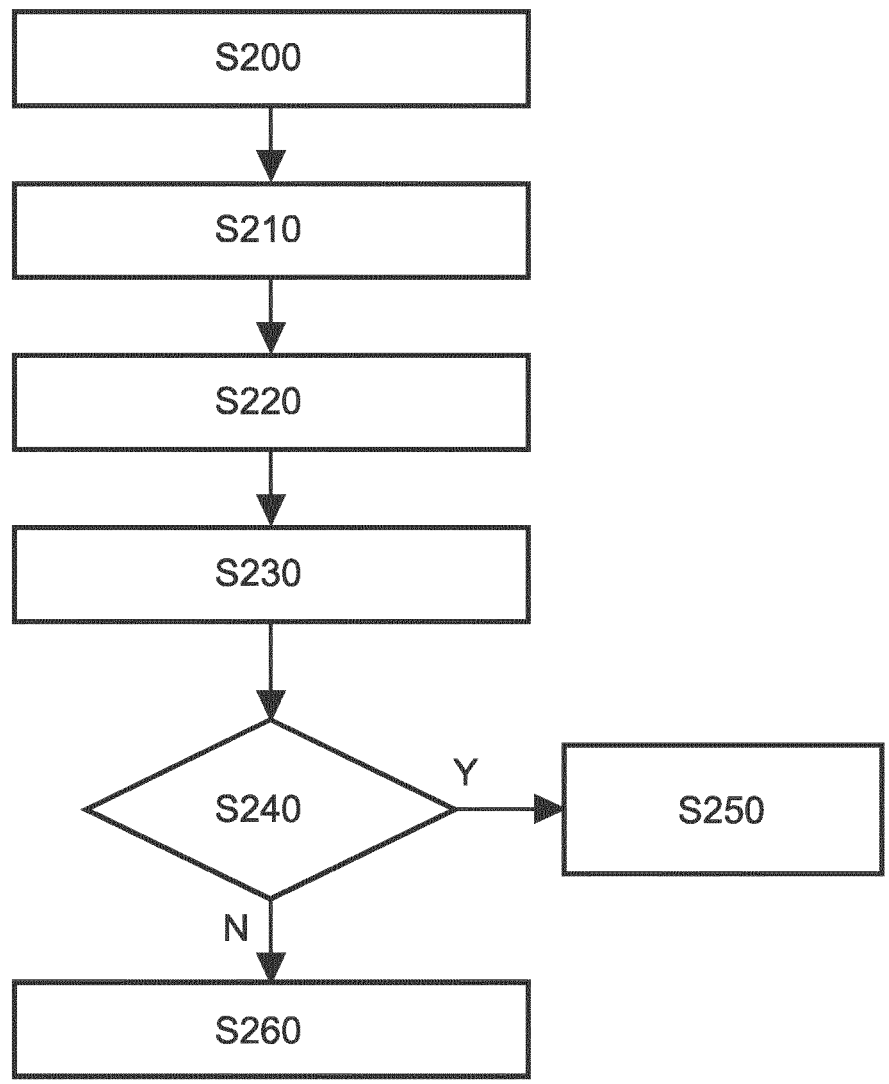
FIG. 2 shows a schematic flow diagram of an automated image analysis procedure according to a first embodiment.

FIG. 2 shows a schematic flow diagram of an automated image analysis procedure according to a first embodiment.

In a first step S200, in order to identify the TZ in the cervix automatically and accurately, a post or pre acetic acid image (where the inner most boarder of the TZ i.e. a new SCJ (Sqamo-columnar Junction) is prominent) is registered with Lugol's iodine image (where outer most border of TZ i.e. an old SCJ is prominent) of the same patient at the same level of magnification using e.g. phase congruency and consistent elastic registration. Multi-stain images (obtained by applying saline, acetic acid and Lugol's iodine) having similar magnification levels are registered, which helps in propagating the anatomical segmentation of different anatomical regions across the stains. More specifically, the TZ (i.e. the region between new SCJ and old SCJ) can be identified by registering at least one Lugol's iodine image and one post acetic acid image (i.e. image after application of acetic acid) or at least one Lugol's iodine image and post saline image (i.e. image after application of saline). The new SCJ identified in post acetic acid or post saline image is mapped to Lugol's Iodine image. Then, the old SCJ is identified in Lugol's iodine image.

Then, in step S210, an aceto-white probable region is identified in the TZ. This can be achieved by using the TZs registered in pre acetic acid (image before application of acetic acid) and post acetic acid images, and identifying those regions that show significant change in whiteness due to the application of acetic acid. Broadly, in the post acetic acid images, pixels in the transformation zone which show dominant opacity changes are identified and they are compared with their corresponding pixels in pre acetic acid image.

FIGS. 5A and 5B show exemplary results of detected and marked aceto-white regions 10.

Once the aceto-white regions are identified in acetic acid images, they are registered in step S220 for further steps using phase congruency and multi stain registration with a corresponding Lugol's iodine image. Both images (i.e. acetic and Lugol's iodine image) are transformed to the phase congruency domain, followed by elastic and consistent registration in the phase congruency domain. This is a special kind of bi-directional registration which consists of combination of elastic image registration based on B-Splines models and consistent image registration. Further details can be gathered from Arganda-Carreras, I., Sorzano, C. O. S., Marabini, R., Carazo, J.-M., Ortiz-de Solorzano, C., and Kybic, J.; "Consistent and elastic registration of histological sections using vector-spline regularization", in Computer Vision Approaches to Medical Image Analysis, Springer, pp. 85-95, 2006. The transformation map of the above transformation to the phase congruency domain is applied in the original image domain to achieve final registration.

Then, in step S230, the Lugol's iodine image is thresholded to separate the regions with mustard yellow and dark brown colour. The main aim of this step is to identify the iodine uptake of the regions in Lugol's iodine image. Thresholding can be applied by considering the red channel of the Lugol's iodine image, plotting a histogram for red channel values, smoothing the histogram, identifying its peaks and valleys, and setting a threshold at the second peak to segment mustard yellow regions.

In step S240 it is determined whether a predetermined percentage (e.g. 80%) of the pixels in aceto-white region correspond to mustard yellow color. If so, then the procedure branches off to step S260 and the iodine uptake is categorized as "iodine negative", else the procedure continues with step S250 and the iodine uptake it is categorized as "iodine positive". If the aceto-white region is identified to be "iodine positive" then it is metaplasia else a premalignant lesion.

FIGS. 6A and 6B show exemplary results of identified iodine uptake 20 by registering aceto-white regions in a Lugol's iodine image.

In the following, two different approaches to demarcate the aceto-white region are explained based on second and third embodiments, respectively.

Figure 3:
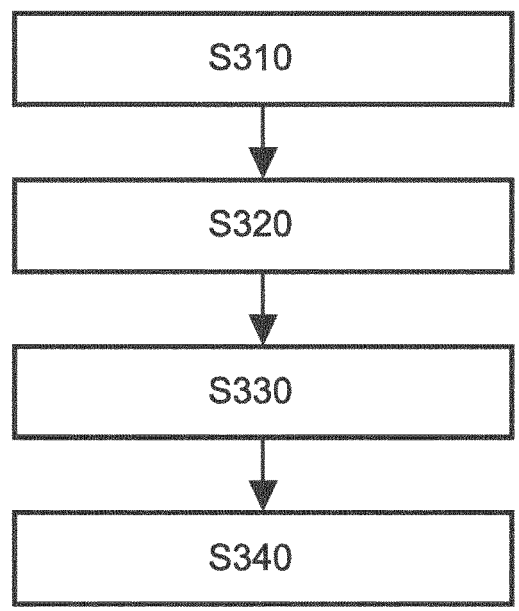
FIG. 3 shows a schematic flow diagram of a clustering based aceto-white region segmentation procedure according to a second embodiment.

FIG. 3 shows a schematic flow diagram of a clustering based aceto-white region segmentation procedure according to the second embodiment.

In step S310, RGB (red, green and blue color) values of the transformation zone in post acetic acid images are converted to the Lab colour space. The Lab color space is a color-opponent space with dimension "L" for lightness and "a" and "b" for the color-opponent dimensions, based on nonlinearly compressed XYZ color space coordinates of the International Commission on Illumination (CIE). The "L" component closely matches human perception of lightness/whiteness. Then, in step S320, pixels are clustered in the transformation zone to two levels of whitish regions, i.e., dominant opacity change and minor opacity change using K-means clustering used to match opaque white and translucent white. K-means clustering is a method of vector quantization and aims at partitioning n observations into k clusters in which each observation belongs to the cluster with the nearest mean, serving as a prototype of the cluster. Thereafter, in step S330, pixels with minor opacity change are removed and finally, in step S340, the corresponding pixels of the dominant opacity change in the pre-acetic acid image are identified.

Figure 4:
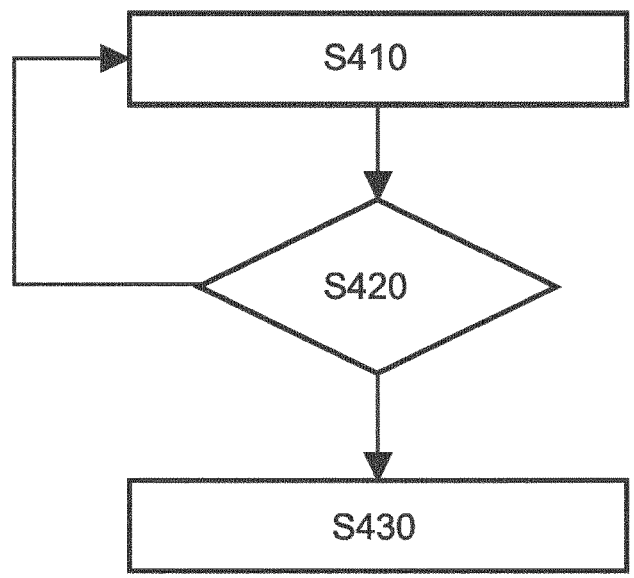
FIG. 4 shows a schematic flow diagram of an information gain based aceto-white region segmentation procedure according to a third embodiment.

FIG. 4 shows a schematic flow diagram of an information gain based aceto-white region segmentation procedure as an alternative approach for aceto-whiteness detection according to a third embodiment.

In step S410, clustering based multilevel histogram thresholding is applied, where a multilevel thresholding process segments grey scale image (inside the TZ region) into several different similar (based on grey scale) regions. The maximum and minimum thresholds are derived from the dataset. Further details are described for example in Seth, S., Naik, S., Jayavanth, S., and Keswarpu, P., "Nucleus Segmentation in Pap-smear Images", ICBME, 2011. This will help in finding the desired result iteratively. However farther steps is needed to terminate the region grow (with the change of threshold) to achieve the aceto-white regions.

Then, in step S420, information gain based aceto-white region segmentation is applied. This information gain based homogeneous region identification serves to isolate aceto-white probable regions. Here, further details are described in Goparaju, S., Acharya, J., Ray, A. K., and Goswami, J. C., "A fast hierarchical multilevel image segmentation method using unbiased estimators", CoRR-Computing Research Repository, 2007. Step S420 is able to bring the suitable termination criteria for step S410 to isolate varied homogeneous regions. The procedure jumps back to step S410 until this termination criteria is met.

Finally, for recognition of aceto-white regions a further step S430 is performed. Namely, feature based aceto-white region selection. Due to the presence of aceto-white appearance, the foreground to background ratio of post acetic image shows a significant increment in intensity when compared to its pre-acetic counterpart. This feature can be leveraged to isolate aceto-white region from its rest.

To summarize, a method and an apparatus for cervical image analysis have been described, wherein a transformation zone is identified in an acetic acid image by registering with its Lugol's iodine counterpart. Then, regions in the transformation zone which show significant changes in whiteness are identified as aceto-white regions and registered with the corresponding Lugol's iodine image, and it is determined if the identified regions in the Lugol's iodine image are iodine negative or positive. Based thereon, the aceto-white region can be categorized as one of metaplasia, inflammation or premalignant lesion region.

While the invention has been illustrated and described in detail in the drawings and foregoing description, such illustration and description are to be considered illustrative or exemplary and not restrictive. The invention is not limited to the disclosed embodiments with the extracted cervix region. The proposed processing can be applied to other regions which can be examined or analyzed with the help of acetic acid and Lugol's iodine image and to any (semi-)automated colposcopy image analysis system that differentiates metaplasia from aceto-whiteness using information from Lugol's iodine images.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

A single unit or device may fulfill the functions of several items recited in the claims. The mere fact that certain measures are recited in mutually different dependent claims does not indicate that a combination of these measures cannot be used to advantage.

The described operations like those indicated in FIGS. 2 to 4 can be implemented as program code means of a computer program and/or as dedicated hardware. The computer program may be stored and/or distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. An apparatus for identifying an aceto-whiteness region, said apparatus comprising:
    a zone identifier configured to identify a transformation zone in an acetic acid image by registering with an iodine counterpart image of said acetic acid image;
    an aceto-white identifier configured to
        identify a region with more than a predetermined minimum change in whiteness within said transformation zone,
        register the identified region with said iodine counterpart image, and
        compare a change of intensity of a foreground to background ratio of a post acetic acid image with that of a pre acetic acid counterpart image; and
    a region separator configured to decide based on said registration of said identified region with said iodine counterpart image on a type of iodine uptake of said identified region so as to determine whether said identified region comprises a premalignant lesion.

2. The apparatus of claim 1, wherein said aceto-white identifier is configured to use transformation zones registered in pre acetic acid and post acetic acid images to identify said region with more than a predetermined minimum change in whiteness due to application of acetic acid.

3. The apparatus of claim 2, wherein said aceto-white identifier is configured to convert color values of an initial color space of said transformation zone in said post acetic acid images to a color space with a color component that substantially matches human perception of lightness or whiteness.

4. The apparatus of claim 2, wherein said aceto-white identifier is configured to
    cluster pixels in said identified transformation zone based on their opacity change and
    remove pixels with an opacity change below a predetermined threshold.

5. The apparatus of claim 1, wherein said aceto-white identifier is configured to apply clustering based multilevel histogram thresholding inside said identified transformation zone.

6. The apparatus of claim 1, wherein said aceto-white identifier is configured to apply information gain based aceto-white region selection.

7. The apparatus of claim 1, wherein said region separator is configured to
    determine a histogram of red channel values of said iodine counterpart image,
    identify peaks of said histogram, and
    determine said type of iodine uptake based on a threshold at a second peak of said histogram.

8. A medical image analysis system comprising the apparatus according to claim 1.

9. A method of identifying an aceto-whiteness region, said method comprising:
- identifying a transformation zone in an acetic acid image by registering with an iodine counterpart image of said acetic acid image, by a zone identifier;
- identifying a region with more than a predetermined minimum change in whiteness within said transformation zone and for registering the identified region with said iodine counterpart image, by an aceto-white identifier;
- compare a change of intensity of a foreground to background ratio of a post acetic acid image with that of a pre acetic acid counterpart image; and
- deciding based on said registration of said identified region with said iodine counterpart image on a type of iodine uptake of said identified region so as to determine whether said identified region comprises a premalignant lesion, by a region separator.

10. A non-transitory computer readable medium comprising computer program code stored thereon, the non-transitory computer readable medium and computer program code being configured to, when run on at least one processor, perform a method of identifying an aceto-whiteness region, the non-transitory computer readable medium comprising:
- instructions for identifying a transformation zone in an acetic acid image by registering with an iodine counterpart image of said acetic acid image, by a zone identifier;
- instructions for identifying a region with more than a predetermined minimum change in whiteness within said transformation zone and for registering the identified region with said iodine counterpart image, by an aceto-white identifier;
- instructions for comparing a change of intensity of a foreground to background ratio of a post acetic acid image with that of a pre acetic acid counterpart image; and
- instructions for deciding based on said registration of said identified region with said iodine counterpart image on a type of iodine uptake of said identified region so as to determine whether said identified region comprises a premalignant lesion, by a region separator, wherein a iodine positive decision determines that the identified region comprises the premalignant lesion.

* * * * *